(12) United States Patent
Quintin et al.

(10) Patent No.: US 8,641,632 B2
(45) Date of Patent: Feb. 4, 2014

(54) METHOD AND DEVICE FOR PREDICTING ABNORMAL MEDICAL EVENTS AND/OR ASSISTING IN DIAGNOSIS AND/OR MONITORING, PARTICULARLY IN ORDER TO DETERMINE DEPTH OF ANESTHESIA

(75) Inventors: Luc Quintin, Lyons (FR); Andrei Cividjian, St Cyr au Mont d'Or (FR)

(73) Assignees: Luc Quintin (FR); Andrei Cividjian (FR)

( * ) Notice: Subject to any disclaimer, the term of this patent is extended or adjusted under 35 U.S.C. 154(b) by 1113 days.

(21) Appl. No.: 11/718,479

(22) PCT Filed: Nov. 3, 2005

(86) PCT No.: PCT/FR2005/050928
§ 371 (c)(1),
(2), (4) Date: Nov. 18, 2008

(87) PCT Pub. No.: WO2006/048587
PCT Pub. Date: May 11, 2006

(65) Prior Publication Data
US 2009/0076339 A1    Mar. 19, 2009

(30) Foreign Application Priority Data
Nov. 3, 2004   (FR) ..................... 04 11726

(51) Int. Cl.
*A61B 5/02* (2006.01)
*A61B 5/04* (2006.01)
(52) U.S. Cl.
USPC ........... 600/483; 600/481; 600/485; 600/509; 600/513
(58) Field of Classification Search
USPC ........... 600/301, 481, 500–509, 483–486, 48, 600/513, 538, 488
See application file for complete search history.

(56) References Cited

U.S. PATENT DOCUMENTS 4,788,982 A * 12/1988 Gedeon et al. ................ 600/483
4,930,517 A *  6/1990 Cohen et al. ................. 600/484
(Continued)

FOREIGN PATENT DOCUMENTS

WO   WO/2004034897 A1   4/2004

OTHER PUBLICATIONS

Jacopo M. Legramante, et al., (1999) "Investigating Feed-Forward Neural Regulation of Circulation From Analysis of Spontaneous Arterial Pressure and Heart Rate Fluctuations" Circulation, vol. 99, No. 13, pp. 1760-1761. XP002334802.

(Continued)

*Primary Examiner* — Navin Natnithithadha
(74) *Attorney, Agent, or Firm* — McDonnell Boehnen Hulbert & Berghoff LLP

(57) ABSTRACT

The invention relates to the field of technological assistance for anaesthesia and intensive care practitioners, as well as to the field of simple, reliable medical monitoring for managing anaesthesia and/or predicting deleterious medical events. The invention aims to provide a system enabling prevention and anticipation of procedures necessary for patients and/or maintenance of patients in a suitable anaesthetic state for a surgical operation at a given time. For this purpose, the invention provides a method of predicting abnormal medical events and/or assisting in diagnosis and/or monitoring, comprising the continuous, real-time detection of a concomitant occurrence of a temporary inefficiency in cardiac baroreceptor reflex and an activation of non-baroreceptor reflex cardiovascular control. The invention also relates to the device used to implement said method.

16 Claims, 5 Drawing Sheets

(56) References Cited

U.S. PATENT DOCUMENTS

| | | | | |
|---|---|---|---|---|
| 6,117,075 | A * | 9/2000 | Barnea | 600/300 |
| 6,120,443 | A * | 9/2000 | Cohen-Laroque | 600/300 |
| 6,371,922 | B1 * | 4/2002 | Baumann et al. | 600/485 |
| 6,421,557 | B1 * | 7/2002 | Meyer | 600/516 |
| 6,522,926 | B1 * | 2/2003 | Kieval et al. | 607/44 |
| 6,685,649 | B2 * | 2/2004 | Korhonen | 600/485 |
| 6,875,418 | B2 * | 4/2005 | Hampton | 424/9.1 |
| 7,158,832 | B2 * | 1/2007 | Kieval et al. | 607/44 |
| 7,499,747 | B2 * | 3/2009 | Kieval et al. | 607/9 |
| 7,623,926 | B2 * | 11/2009 | Rossing et al. | 607/44 |
| 7,874,992 | B2 * | 1/2011 | Cho et al. | 600/483 |
| 8,109,879 | B2 * | 2/2012 | Zhang et al. | 600/483 |
| 2002/0058877 | A1 * | 5/2002 | Baumann et al. | 600/485 |
| 2004/0254616 | A1 * | 12/2004 | Rossing et al. | 607/42 |
| 2006/0004417 | A1 * | 1/2006 | Rossing et al. | 607/9 |
| 2006/0074453 | A1 * | 4/2006 | Kieval et al. | 607/9 |
| 2006/0094967 | A1 * | 5/2006 | Bennett et al. | 600/508 |
| 2007/0112275 | A1 * | 5/2007 | Cooke et al. | 600/513 |
| 2007/0161912 | A1 * | 7/2007 | Zhang et al. | 600/483 |

OTHER PUBLICATIONS

Gerfried Gratze, et al., (1998) "A software package for non-invasive, real-time beat-to-beat monitoring of stroke volume, blood pressure, total peripheral resistance and for assessment of autonomic function" Computer in Biology and Medicine, vol. 28, No. 2 pp. 121-141. XP004532373.

Nosaka S, "Modifications of Arterial Baroreflexes: Obligatory Roles in Cardiovascular Regulation in Stress and Poststress Recovery", Japanese Journal of Physiology, 46, (1996), pp. 271-288.

Smyth, Harley S., "Reflex Regulation of Arterial Pressure during Sleep in Man: a Quantitative Method of Assessing Baroreflex Sensitivity", Circulation Research, 24, (1969), pp. 109-121.

* cited by examiner

METHOD AND DEVICE FOR PREDICTING ABNORMAL MEDICAL EVENTS AND/OR ASSISTING IN DIAGNOSIS AND/OR MONITORING, PARTICULARLY IN ORDER TO DETERMINE DEPTH OF ANESTHESIA

The field of the invention covers the field of the technological assistance for anesthesia or intensive care practitioners, together with the field of simple and reliable medical monitoring for anesthesia management and/or for prediction of deleterious medical events. The objectives targeted are notably the anticipation of the necessary care for the patients and/or the maintenance of the patients in the anesthetized state adequate for the surgical procedure at the moment in question.

More precisely, the invention relates to a method and a device for predicting abnormal medical events and/or for assisting in diagnosis and/or monitoring, in particular for the determination of the depth of anesthesia.

Other objectives of the invention are the algorithms and the computer programs for the implementation of the method.

General anesthesia may be defined as a pharmacologically induced state of unconsciousness, in which the patient does not feel (analgesic) and does not remember (amnesic) the painful stimulation. Such an anesthesia may be considered as "adequate" or sufficiently "deep". The anesthesia has at least two components: on the one hand, the hypnotic component that ensures the loss of consciousness and the amnesia and, on the other, the analgesic component. In spite of the large number of general anesthesias that take place annually throughout the world (more than 50 million in the developed countries), much progress still remains to be made in order to improve the safety of patients and the work of the specialists.

Indeed, in order to ensure the adequacy of the anesthesia, the anesthetic dose must be continuously adjusted, varying according to the biological variability of the patient and according to the intensity of the painful stimulation. Currently, the adjustment of the anesthetic dose is made according to traditional clinical signs which are not sufficiently reliable: hypertension, tachycardia, lacrimation, motor response to painful stimulation, etc. For this reason, a monitor of the depth of the anesthesia would be required for precise dosage of the anesthetic, thus avoiding the risk of over- or under-dosage.

An anesthetic under-dosage leads to a risk of accidental waking during the operation. In any precision surgery, intra-operative involuntary movements can lead to deleterious consequences. In addition, an accidental intra-operative waking presents a risk of recall and of post-traumatic neurosis.

An anesthetic over-dosage increases the cardiovascular or respiratory risks, and also the recovery time. This slows down the rotation of operating theaters and recovery rooms.

Monitors of the hypnotic component of the anesthesia currently exist. These monitors are based on either the electroencephalogram (EEG) or on the auditory evoked potentials. Thanks to these monitors which essentially record the regions of the cerebral cortex, the occurrences of intra-operative recall can be considerably reduced. However, the problem of intra-operative involuntary movements remains unresolved up to now. Indeed, the intra-operative involuntary movement is more likely to be associated with the analgesic component than with the hypnotic component of the anesthesia. The cardiovascular signals could be indicators of the activity of the sub-cortical regions (hypothalamus, peri-aquaductal gray matter, vasomotor center) that could receive and generate more precocious indicators of the lightening of the anesthesia than the cortical regions. In this context, a monitor for the lightening of the anesthesia, based on cardiovascular signals, would be of great interest notably for the prediction of intra-operative involuntary movement.

Beyond this precise problem of involuntary movement, a constant need exists for methods and devices:
for assisting with diagnosis in real time in intensive cardiology care or in mobile cardiology (forecast of myocardic ischemia or of ventricular fibrillation),
monitoring of the anesthesia for factors other than the depth of anesthesia and the prediction of waking (post-operative myocardic ischemia, local/regional anesthesia, pain, etc. . . . ),
for medical or surgical resuscitation (adult, pediatric, neonatal),
for obstetrics,
for accident and emergency medicine, oxyology,
for medicine in space,
for functional exploration of the autonomic nervous system (stroke, diabetes, neuro-vegetative dystonia . . . ).

The means of assistance expected by practitioners ought to allow them to have sufficient early warning of the occurrence of abnormal phenomena in the patient, in order to deal effectively with these phenomena and with their consequences.

It is desirable that the data transmitted to the practitioners be simple and easy to read, to interpret and to utilize.

A monitoring method and a monitoring device are known called TASK-FORCE MONITOR 3040, developed and marketed by the Austrian company CNSystems. The TASK-FORCE MONITOR comprises a software part and a hardware part. The latter includes signal sensors and a computer equipped with a display screen showing up to 14 parameters.

This method and this device of the prior art are described notably in the article "Gratze et al., *Computers in Biology and Medicine*, 1998, vol. 28, 121-142". This software and its peripheral devices aim to provide a non-invasive monitoring in real time, beat-by-beat, of the systolic ejection volume, of the blood pressure and of the total peripheral resistance index. One objective targeted by this system is the evaluation of the activity of the autonomic nervous system which controls the operation of the heart.

The device TASK-FORCE MONITOR comprises sensors for the measurement of the blood pressure measured by means of an armband (DINAMAP®), of the arterial pressure measured by finger (FINAPRES®), of the electrocardiogram ECG, of the impedance cardiogram ICG and of the phonocardiogram PCG.

The software implements algorithms for calculating the interval RR between two QRS complexes of the ECG, the systolic arterial pressure SAP, the diastolic arterial pressure, the mean arterial pressure, the ejection volume and the total peripheral resistance index.

These hemodynamic parameters are obtained from the analog signals measured continuously and in real time on the patients, then digitized.

According to this prior art, the spectral analysis of the interval RR of the SAP, of the diastolic pressure, of the mean arterial pressure, of the systolic ejection volume and of the total peripheral resistance index is carried out continuously and in real time. The drawback with this technique is, firstly, that it requires stationary data, which is often not the case, especially in the course of a surgical procedure under general anesthesia. Secondly, this technique disregards the pulsating component of the vascular function.

The hemodynamic data measured or calculated are also used for the automatic calculation of the sensitivity of the baro-reflex of the patient. The algorithm implemented seeks the episodes of spontaneous activity of the baro-reflex. These episodes are defined as corresponding to the case where the interval RR gets wider following an increase in the SAP (+/+ sequence) or the interval RR gets smaller following a decrease in the SAP (−/− sequence), according to amplitudes of at least 4 milliseconds for the interval RR and of at least one millimeter of mercury for the SAP, respectively, during at least 4 consecutive heart beats. The linear regressions of the increases/decreases in the SAP and of the simultaneous increases/decreases in the interval RR are calculated. The algorithm then determines the mean of the linear regressions thus obtained, which gives an average slope (ms/mm Hg) corresponding to the sensitivity of the baro-reflex. A patient whose autonomic nervous system is affected exhibits a reduced sensitivity of the baro-reflex with respect to a normal subject.

This article does not refer to a continuous surveillance in real time of the concomitant occurrence of a temporary inefficiency of the cardiac baro-reflex and of an activation of the non-baro-reflex cardiovascular regulation, as predictive indicator of medical events (e.g. waking from anesthesia), requiring an appropriate medical response.

The article by "Legramente et al., *Circulation*, 1999, vol. 99, 1761-1766" demonstrates that there exist, with regard to neuro-regulation of the circulation, non-baro-reflex sequences with feed-forward comprising at least 3 beats, in which a reduction in the interval RR with a simultaneous increase in the SAP (−/+) occurs. According to the authors of this article, these non-baro-reflex sequences are the expression of a short-term cardiovascular regulation with integrated feed-forward and under nerve influence. This regulation is capable of dynamically interacting with the feed-back mechanisms of baro-reflex origin in the control of the cardiac frequency. These non-baro-reflex sequences are under the influence of the sympathetic and parasympathetic nervous systems.

The article by Legramente et al. does not provide any indication regarding the use of non-baro-reflex sequences RR(−)/SAP(+) as a continuous predictive signal in real time of abnormal events for patients under tighter surveillance (anesthesia, intensive care, etc.) in this respect. On the contrary, Legramente puts forward the hypothesis that, under normal conditions, the neuronal mechanisms responsible for a feed-forward regulation could be in continual opposition with the mechanisms of the baro-reflex responsible for a feed-back regulation. In addition, Legramente does not disclose the filtering process of the signals RR or SAP.

The U.S. Pat. No. 5,437,285 describes a method and a device for predicting sudden cardiac death, by simultaneous evaluation of the influence of the autonomic nervous system on the heart and of the cardiac electric stability.

VERRIER and NEARING, the inventors cited in this patent, fixed themselves the objective of perfecting a non-invasive dynamic method for assessing the vulnerability of patients with regard to ventricular fibrillation.

For this purpose, the alternation of the T wave, the variability of the heart rhythm and the size of the dispersion of the interval QT are simultaneously evaluated. This evaluation is carried out beat-by-beat, within the successive intervals RR. The algorithm used therefore creates a series of intervals RR that form a signal RR.

The variability of the heart rhythm is estimated by calculating the low-frequency components around 0.1 Hz (LF), the high-frequency components around 0.35 Hz (HF), together with the ratio LF/HF within the spectrum of the cardiac frequency calculated beat-by-beat.

The method according to this patent also proposes the measurement of the sensitivity of the baro-reflex. This parameter is obtained from the arterial pressure, from the instantaneous cardiac frequency and from a signal representing the instantaneous pulmonary volume, by means of a technique based on an autoregressive moving average (ARMA) model.

This patent does not refer to a continuous surveillance in real time of the concomitant occurrence of a temporary inefficiency of the cardiac baro-reflex and of an activation of the non-baro-reflex cardiovascular regulation, as predictive indicator of medical events (e.g. waking from anesthesia), requiring an appropriate medical response.

The U.S. Pat. No. 5,419,338 relates to a method and a device for detecting imbalances in the control of the cardiovascular system by the parasympathetic/sympathetic autonomic nervous system. This is a direct method for evaluating imbalances of the sympathetic/parasympathetic controls and for indicating the predispositions to sudden cardiac death. According to these documents, the variability of the interval QT simultaneous with the variability of the interval RR is analyzed, and the spectral analysis of the signals RR and QT is then performed. The indicator of the imbalances in the nervous system must be autonomous and given by the analysis of the QT versus RR frequency densities. It is clear that this document does not refer to a continuous surveillance in real time of the concomitant occurrence of a temporary inefficiency of the cardiac baro-reflex and of an activation of the non-baro-reflex cardiovascular regulation, as predictive indicator of medical events (e.g. waking from anesthesia), requiring an appropriate medical response.

The U.S. Pat. No. 5,967,995 describes a system for the prediction of high-risk cardiac arythmias. According to this method, the signal RR is decomposed and transformed into KARHUNEN LOEVE transformation coefficients. It is these coefficients that are used as predictive indicators for cardiac accidents. This method involves the spectral analysis of the signal RR.

This US patent does not refer to a continuous surveillance in real time of the concomitant occurrence of a temporary inefficiency of the cardiac baro-reflex and of an activation of the non-baro-reflex cardiovascular regulation, as predictive indicator of medical events (e.g. waking from anesthesia), requiring an appropriate medical response.

The application PCT WO-A-95/03739 discloses a method for measuring the activity of the autonomic nervous system, according to which a series of intervals RR are continuously measured using an ECG and a Poincaré representation is continuously constructed from the continuous intervals RR in real time. The level of the sympathetic activity of the patient can be quantified by determining the correlation dimension corresponding to the Poincaré graphical representation. The level of cardiac disorder is appreciated by observing to what extent the correlation dimension is outside of a pre-determined interval. The level of parasympathetic activity may also be quantified from the width of the set of points of the Poincaré representation. This prior art technical teaching does not refer to a continuous surveillance in real time of the concomitant occurrence of a temporary inefficiency of the cardiac baro-reflex and of an activation of the non-baro-reflex cardiovascular regulation, as predictive indicator of medical events (e.g. waking from anesthesia), requiring an appropriate medical response.

The U.S. Pat. No. 5,439,004 relates to a system and a method for detecting ventricular fibrillations based on chaos theory. According to this method, a Poincaré representation of the amplitude of the ECG signal is employed. This prior art technical teaching does not refer to a continuous surveillance in real time of the concomitant occurrence of a temporary inefficiency of the cardiac baro-reflex and of an activation of the non-baro-reflex cardiovascular regulation, as predictive indicator of medical events (e.g. waking from anesthesia), requiring an appropriate medical response.

The French patent FR-B-2747027 discloses a method and a device for determining the depth of anesthesia for a patient to whom at least one anesthetizing product is administered, comprising a step (10) for acquisition of at least one signal representative of the activity of the heart of the patient, a step (12) for detecting the position of a given periodic wave within each signal from the heart of the patient, a step (13) for calculating time intervals between said periodic waves, a step (14) for determining a numerical series of time intervals, a step (15) for calculating one fractal dimension from said series of time intervals and a step (16) for calculating the depth of anesthesia as a function of the fractal dimension.

The step (10) for the acquisition of at least one signal consists in measuring at least one—or even at least two—of the following signals from the patient: the electrocardiogram, the blood flow rate, the light absorption by the blood, the arterial pressure, the oxygen concentration in the blood or else an acoustic signal emitted by the heart. The step (15) for calculating a fractal dimension of said series of time intervals consists in calculating a correlation dimension of these series. The step (16) for calculating the depth of anesthesia as a function of the fractal dimension consists in determining the fractal dimension of numerical series of time intervals prior to the administration of at least one anesthetizing product to the patient, in defining a normalization coefficient such that the product of this coefficient with the fractal dimension is substantially equal to a reference value and in multiplying the fractal dimension of series of time intervals, after the administration of at least one anesthetizing product to the patient, by the normalization coefficient.

This prior art technical teaching does not refer to a continuous surveillance in real time of the concomitant occurrence of a temporary inefficiency of the cardiac baro-reflex and of an activation of the non-baro-reflex cardiovascular regulation, as predictive indicator of medical events (e.g. waking from anesthesia), requiring an appropriate medical response.

The U.S. Pat. No. 5,372,140 discloses a method and an apparatus for measuring the depth of the anesthesia in real time by measuring the sinusal arythmia. According to this method, the series of the intervals RR are analyzed in order to determine the position in time of each R wave with respect to the respiratory cycle. If the respiratory cycle is represented in the form of a circle, a position on this circle is associated with each R wave, together with a vector whose origin is in the center of the circle and which is oriented toward the position of the R wave on the circle. A resultant vector is calculated and then compared with a reference vector in order to derive an index for the depth of the anesthesia. The reference vector is calculated by means of the Reyleigh test as a function of a pre-defined probability level which can be selected by the user. The method uses as input signals the electrocardiogram and a respiratory signal. This prior art technical teaching does not refer to a continuous surveillance in real time of the concomitant occurrence of a temporary inefficiency of the cardiac baro-reflex and of an activation of the non-baro-reflex cardiovascular regulation, as predictive indicator of medical events (e.g. waking from anesthesia), requiring an appropriate medical response.

The U.S. Pat. No. 6,685,649 discloses a method of monitoring the state of the patient under anesthesia or sedation. According to this method, a signal (S) is acquired that represents the cardiovascular activity of the patient. The signal (S) can preferably be the electrocardiogram, but also the arterial pressure, the concentration of oxygen in the blood, etc. Repetitive waves (P) are detected within the signal (S) and the calculation of the time intervals (Ti) or pressures (Bi) or time frequencies (Ri) is carried out using these successive waves. The temporal series of the intervals (Ti) or of the pressures (Bi) or of the frequencies (Ri) are filtered giving rise to averaged series. This filtering eliminates the rapid variations controlled by the parasympathetic system. The presumed activations of the sympathetic system are subsequently sought within the averaged series by detecting substantial decreases in the time intervals (e.g. intervals RR) or, alternatively, substantial increases in the cardiac frequency or substantial increases in the arterial pressure (e.g. systolic arterial pressure). The detection of the decreases, or the increases, respectively, of the averaged signals is performed by calculating the derivative of the averaged series. In the series of the derivatives of the averaged series, the derivatives corresponding to sympathetic cardiovascular activations are accentuated, whereas the other derivatives are eliminated or neglected by means of a mathematical operator. In the series of the derivatives thus selected, called accelerations, a moving average is applied giving rise to an acceleration index (e.g. acceleration index of the cardiac frequency). The acceleration index is, according to the inventor, an index of the adequacy of the analgesic for patients under general anesthesia or sedation. The index of the acceleration of the cardiac frequency has recently been coupled with the index of the entropy of the frontal electromyogram (Rantanen, M. et al. *Anesthesiology*, 2004, vol. 101: A559). This prior art technical teaching does not refer to a continuous surveillance in real time of the concomitant occurrence of a temporary inefficiency of the cardiac baro-reflex and of an activation of the non-baro-reflex cardiovascular regulation, as predictive indicator of medical events (e.g. waking from anesthesia), requiring an appropriate medical response.

Methods based on the electroencephalogram (EEG) or the auditory evoked potentials have been recently developed and measure the hypnotic component of the anesthesia. The indices derived from the EEG reflect the activity of the cerebral cortex. The most well-known index derived from the EEG is the Bispectral Index (BIS®, Aspect, Natick, Mass.) the initial idea of which was disclosed by the U.S. Pat. No. 4,907,597. Other indices exist also based on the EEG, such as a) the spectral edge frequency (SEF) or the median frequency (MF) from the EEG spectrum, b) the patient state index (PSI, Physiometrix, N. Billerica, Mass.), c) the entropy of the EEG (M-Entropy index, S/5 Entropy Module, Datex-Ohmeda, Helsinki, Finland), d) the Narcotrend index (Hamburg, Germany), e) the Lempel-Ziv complexity of the EEG, etc.

The auditory evoked potentials are measured by means of the AAI index (A-line ARX Index) calculated in real time by the A-Line® monitor (Danmeter, Odense, Denmark). The AAI index reflects a mixture of the cortical and sub-cortical activity. However, the performance of the AAI index is as poor as the BIS index for predicting the intra-operative movement in response to a nociceptive stimulus (Struys, M. M. et al. *Anesthesiology*, 2002, vol. 96: 803-816): the motor response to a nociceptive stimulus could be the effect of a spinal reflex rather than a supra-spinal one. In general, the monitors based on the spontaneous EEG or evoked potentials do not perform well for the evaluation of the analgesia, their index often increasing at the same time as or even after the occurrence of the intra-operative movement.

In order to overcome the deficiency of the prior art, one of the essential objectives of the invention is to provide a method and a device that perform well, are low-cost and simple, "allowing the reliable and certain prediction of" the occurrence of unforeseen medical events (e.g. unexpected intra-operative movement in response to a nociceptive stimulation, wakening from anesthesia, lightening of the general anesthesia, notably of the analgesic component, etc.), requiring an appropriate medical response.

Another essential objective of the invention is to provide a method and a device for simple, reliable, low-cost and adequate monitoring of the anesthesia in such a manner as to allow surgical interventions to be performed in an optimized manner under general anesthesia while avoiding any problems of over-dosage or under-dosage of anesthetics.

Another essential objective of the invention is to provide a method and a device that are reliable, high-performance and low-cost, notably:

- for assisting with diagnosis in real time in intensive cardiology care or in mobile cardiology (forecast of myocardic ischemia or of ventricular fibrillation),
- monitoring of the anesthesia for factors other than the depth of anesthesia and the prediction of waking (post-operative myocardic ischemia, local/regional anesthesia, pain, etc. . . . )
- for medical or surgical resuscitation (adult, pediatric, neo-natal),
- for obstetrics,
- for accident and emergency medicine, oxyology,
- for medicine in space,
- for functional exploration of the autonomic nervous system (stroke, diabetes, neuro-vegetative dystonia . . . ).

These objectives, amongst others, have been achieved by the invention whose subject is firstly a method for predicting abnormal medical events and/or for assisting in diagnosis and/or for monitoring, characterized in that it consists essentially in detecting, continuously and in real time, the concomitant occurrence of a temporary inefficiency of the cardiac baro-reflex and of an activation of the non-baro-reflex cardiovascular regulation.

Another subject of the invention is a device, in particular for the implementation of above said method, characterized in that it comprises means for detecting, continuously and in real time, the concomitant occurrence of a temporary inefficiency of the cardiac baro-reflex and of an activation of the non-baro-reflex cardiovascular regulation.

After long and involved research efforts, the inventors have succeeded in demonstrating that it is possible to use any concomitant occurrence of a temporary inefficiency of the cardiac baro-reflex and of an activation of the non-baro-reflex cardiovascular regulation as predictive indicator of abnormal medical events. In other words, according to the invention, the concomitant occurrence of a temporary inefficiency of the cardiac baro-reflex and of an activation of the non-baro-reflex cardiovascular regulation is equated, for example, to an index for the lightening of the analgesic component of the anesthesia and for the prediction of involuntary intra-operative movement.

More precisely, the invention consists in selecting particular instantaneous cardiovascular signals in order to demonstrate such a concomitant occurrence of a temporary inefficiency of the cardiac baro-reflex and of an activation of the non-baro-reflex cardiovascular regulation.

Thus, preferably, the method according to the invention comprises the following steps:

a. continuous measurement (beat-by-beat) of the time intervals between 2 consecutive cardiac cycles (IT) and of the arterial pressure (AP);
b. filtering by means of a low-pass filter of the beat-by-beat series of the time intervals IT and of the series of AP calculated at step a), in order to eliminate the rapid variations under parasympathetic control, at the upper respiratory frequency or the frequency equal to a threshold in the range between 0.1 and 0.15 Hz, this filtering giving rise to filtered series $IT_f$ and $AP_f$ of IT and of AP, respectively;
c. surveillance of the concomitant occurrence of a temporary inefficiency of the cardiac baro-reflex and of an activation of the non-baro-reflex cardiovascular regulation via the manifestation of events chosen from the following group of sequences:
  - increase in $AP_f$/time period/reduced increase in $IT_f$;
  - increase in $AP_f$/time period/delayed increase in $IT_f$;
  - increase in $AP_f$/time period/decrease in $IT_f$;
  - and also the combination of at least two of these sequences;
d. emission of an alarm for warning of the concomitant occurrence of a temporary inefficiency of the cardiac baro-reflex and of an activation of the non-baro-reflex cardiovascular regulation according to step c).

Preferably, the device according to the invention essentially comprises:

(a) means for continuously measuring (beat-by-beat) time intervals between 2 consecutive cardiac cycles (IT) and of the arterial pressure (AP);
(b) a low-pass filter for filtering beat-by-beat series of the time intervals IT and of the AP series previously measured, in order to eliminate the rapid variations under parasympathetic control, at the upper respiratory frequency or the frequency equal to a threshold in the range between 0.1 and 0.15 Hz, this filtering giving rise to filtered series $IT_f$ and $AP_f$ of IT and of AP, respectively;
(c) surveillance means for monitoring the concomitant occurrence of a temporary inefficiency of the cardiac baro-reflex and of an activation of the non-baro-reflex cardiovascular regulation via the manifestation of events chosen from the following group of sequences:
  - increase in $AP_f$/time period/reduced increase in $IT_f$;
  - increase in $AP_f$/time period/delayed increase in $IT_f$;
  - increase in $AP_f$/time period/decrease in $IT_f$;
  - and also the combination of at least two of these sequences;
(d) and at least one alarm for warning of the concomitant occurrence of a temporary inefficiency of the cardiac baro-reflex and of an activation of the non-baro-reflex cardiovascular regulation.

The time intervals IT are, preferably, calculated from the intervals RR, in other words time intervals between two QRS complexes of the ECG, either from the intervals between two points that are characteristic (start points of rise or maxima or others) of the continuous AP or of the continuous oxygen saturation level of the blood (SpO2).

Advantageously, the device of the invention comprises means for calculating the intervals IT as explained in the preceding paragraph.

The AP is chosen from the group of signals comprising: the systolic arterial pressure (SAP) of the patient, the diastolic arterial pressure (DAP) of the patient, the mean arterial pressure (MAP) of the patient, the SAP being preferred.

The continuous AP is preferably obtained either by direct invasive or non-invasive measurement, or by indirect measurement preferably using the continuous SpO2, calibrated by means of the intermittent values of AP preferably obtained by means of a blood-pressure armband.

Advantageously, the device of the invention comprises means for measuring the continuous AP, these means operating as is explained in the preceding paragraph.

In the case where the series of continuous AP are obtained in an indirect manner by means of the continuous SpO2 calibrated with the intermittent values of AP, the method according to the invention preferably comprises the following steps:

a1) the series of the maxima of the SpO2 signal during each cardiac cycle is calculated;
a2) the series obtained at step a1) is inverted by subtracting from a constant strictly higher than the maximum amplitude of the SpO2 signal;
a3) calibration of the series obtained at step a2) in units of pressure by applying a linear operator of the $1^{st}$ degree to the series obtained at step a2), the coefficients of this operator being obtained from the intermittent values of AP.

The device according to the invention advantageously comprises the calculation means, the viewing means and the means for calibrating the series, in order to allow the implementation of steps a1), a2) and a3), respectively, described above.

The series IT and SAP exhibit continual variations of at least 3 types:
a) associated with the respiration (>0.1 Hz), eliminated according to the invention by a filter,
b) around 0.1 Hz (Mayer waves) and
c) slower.

The rapid variations associated with the respiration are under parasympathetic control. By eliminating them during the low-pass filtering, only the variations under sympathetic control remain to be analyzed.

The low-pass filtering of the series of IT and of AP is preferably carried out in real time by means of at least one filter with infinite pulse response (RII) or with finite pulse response, or by means of any other type of low-pass filter with good performance, the filter of the RII type being preferred.

The device of the invention advantageously comprises at least one filter such as is defined in the preceding paragraph.

So that the practitioners are informed quickly and clearly, the invention preferably provides for at least one of the following signals to be displayed on at least one screen: the series of IT and of AP obtained according to the point a) and the series of $IT_f$ and $AP_f$ obtained according to the point b).

The device of the invention advantageously comprises at least one screen allowing the signals defined in the preceding paragraph to be displayed.

Normally, by virtue of a feed-back regulation, the cardiac baro-reflex makes a bradycardia, in other words increases in the time intervals IT, correspond to rise points in the SAP, after a variable delay (1-20 s). Generally speaking, during a lightening of the anesthesia (notably of the analgesic component) the patient begins to feel pain following nociceptive stimulations, initially at the level of the subconscious, then later on at the conscious level upon complete emergence. The afferent channels of the nociception project onto the sub-cortical regions such as the hypothalamus or the peri-aquaductal gray matter. An activation of these sub-cortical regions results in a tachycardia and a hypertension induced by non-cardiovascular afferents that come and occlude the baro-reflex arc. Consequently, the bradycardia induced by the baro-reflex arc following a rise in pressure is in continuous competition with a possible non-baro-reflex tachycardia induced by the above-mentioned sub-cortical regions following the nociceptive stimulus. A baro-reflex/non-baro-reflex equilibrium exists at all times.

During a lightening of the anesthesia (notably of the analgesic component), episodes of short duration exist during which the operation of the baro-reflex is occluded by a non-baro-reflex function according to the following: the rise points in the SAP are followed either by a very small rise in the IT (baro-reflex not very efficient), or by a delayed rise in the IT (delayed baro-reflex), or by a decrease in the IT (tachycardia indicating a non-functional baro-reflex, occluded by a non-baro-reflex cardiovascular regulation), which is the reverse of the expected functioning of the cardiac baro-reflex. This lightening of the anesthesia is generally the cause of the involuntary intra-operative movement following a nociceptive stimulation.

One of the strong points of the invention is notably to have isolated and quantified this concomitant occurrence of a temporary inefficiency of the cardiac baro-reflex and of an activation of the non-baro-reflex cardiovascular regulation, in real time by means of an algorithm capable of triggering an alarm.

The concomitant occurrence of a temporary inefficiency of the cardiac baro-reflex and of an activation of the non-baro-reflex cardiovascular regulation is preferably effected by means of at least four following parameters:

p1) the ratio between the area under the curve of a sequence of $IT_f$ called baro-reflex response of $IT_f$ and the area under the curve of the rise in $AP_f$ which has caused said baro-reflex response of $IT_f$;
p2) the amplitude of the fall in $IT_f$ which has preceded the rise in $IT_f$ that follows said rise in $AP_f$;
p3) the ratio between the amplitude of said baro-reflex response of $IT_f$ and the amplitude of said fall in $IT_f$;
p4) the algebraic difference $\Delta IT$ between the value of $IT_f$ after a period of time referred to as estimation time starting from the beginning of said baro-reflex response of $IT_f$ and the value of $IT_f$ at the start of said baro-reflex response of $IT_f$;

and also any combination, weighted or not, of the preceding parameters.

In the device of the invention, the surveillance means (c) advantageously implement at least the four parameters p1), p2), p3) and p4) defined in the preceding paragraph.

In the method or the device according to the invention, the baro-reflex response of $IT_f$ caused by a rise in $AP_f$ is preferably:
either the rise in $IT_f$ that follows said rise in $AP_f$ if said rise in $IT_f$ begins within an interval of time included between a lower limit equal to 0 s and an upper limit included between 10 s and 20 s with respect to the start of said rise in $AP_f$;
or the sequence of $IT_f$ which begins after an interval of time included between 5 s and 15 s with respect to the start of said rise in $AP_f$, in the case where the rise in $IT_f$ that follows said rise in $AP_f$ begins after said upper limit in the range between 10 s and 20 s with respect to the start of said rise in $AP_f$;
in both cases, the duration of the baro-reflex response of $IT_f$ being equal to said estimation period; the amplitude of said baro-reflex response of $IT_f$ being the difference between the maximum reached by the $IT_f$ in the course of its rise over the duration of said baro-reflex response of $IT_f$ and the level of $IT_f$ at the start of the rise in $IT_f$ that follows said rise in $AP_f$.

In the method or the device according to the invention, the rises in $AP_f$ taken into consideration are preferably those whose amplitude is higher than a pressure threshold in the range between 1 mmHg and 5 mmHg, preferably between 2 mmHg and 4 mmHg, or even better between 2 mmHg and 3 mmHg, the other rises in $AP_f$ being neglected.

In the method or the device according to the invention, the period called estimation period is preferably equal to the duration of said rise in $AP_f$ multiplied by a coefficient in the range between 0.5 and 2, preferably between 1 and 1.8.

Preferably, said areas under the curves of the baro-reflex response of $IT_f$ and of the rise of $AP_f$ are calculated between a time called reference time and during said estimation period by performing, for each sample of said curve in the course of said estimation period starting from said reference time, the sum of the algebraic differences between the value of the sample at a given moment and the value of the curve at said reference time. Since they are algebraic sums, said areas may be either positive or negative.

The device according to the invention advantageously comprises means for calculating the above-mentioned areas, these means operating as explained in the preceding paragraph.

Other known cardiovascular parameters that are applicable to the signals IT or AP as a function of time may be used in combination with the parameters p1-p4, such as the ratio between the low- and high-frequency powers (LF/HF), alpha coefficient, coherence, analyses using the Poincaré representation, fractal dimension, beta slope, non-linear analysis, time-frequency analysis, wavelet analysis, as an indicator of a baro-reflex inefficiency and/or of a sympathetic activation and/or of a parasympathetic inhibition under the control of the sub-cortical regions stimulated by the nociceptive receptors.

Preferably, at least one alarm (d) is designed to predict any lightening, programmed or inopportune, of the anesthesia, notably of the analgesic component. This alarm, designed to warn of the concomitant occurrence of a temporary inefficiency of the cardiac baro-reflex and of an activation of the non-baro-reflex cardiovascular regulation, according to step d), is raised by continuously displaying in real time a predictive index expressing the cardiovascular depth of the anesthesia (CARDEAN©: Cardiovascular Depth of Anesthesia).

The device according to the invention advantageously comprises at least one alarm and means for displaying this alarm, as explained in the preceding paragraph.

The index of the depth of the anesthesia according to the invention is used, preferably, only from the moment where the patient is already anesthetized and all Guedel signs are inhibited, namely the ciliar reflex, the corneal reflex, the lacrimation, the eye movement and the motor response to the nociceptive stimulation.

Step c) of the surveillance for the concomitant occurrence of a temporary inefficiency of the cardiac baro-reflex and of an activation of the non-baro-reflex cardiovascular regulation, together with the emission of an alarm according to step d), are preferably alternately governed by at least one of the following algorithms:

A1) the predictive index expressing the cardiovascular depth of the anesthesia indicates a lightening of the anesthesia, notably of the analgesic component, and emits an alarm when at least the four following conditions are met:

the parameter p1 is below a threshold s1 in the range between 0 and 4, preferably between 1 and 3, the parameter p2 is above a threshold s2 in the range between 30 ms and 300 ms, preferably between 40 ms and 80 ms, the parameter p3 is below a threshold s3 in the range between 0 and 1, preferably between 0.25 and 0.75, preferably between 0.3 and 0.75, the parameter p4 is below a threshold s4 in the range between −100 and 25, preferably between −40 and 10, preferably between −20 and 10, or, A2) the predictive index, expressing the cardiovascular depth of the anesthesia and indicating a lightening of the anesthesia, notably of the analgesic component, and emitting an alarm, is obtained by using a neural network having as input parameters the parameters of p1 to p4, and having learning conditions so as to obtain an optimal combination of sensitivity and selectivity, by means of an ROC (Receiver Operator Characteristic) curve.

Advantageously, the surveillance means (c) of the device according to the invention and the alarm (d) are governed by A1) or A2), as is defined hereinabove.

According to another of its aspects, the invention relates to a computer program, in particular for the implementation of the method such as is defined above or for governing the means (c) and the alarm (d) of the device such as is defined above. This method is characterized in that it comprises program code means for performing the totality of the steps of the algorithm(s) A1) and/or A2) such as is/are defined hereinabove, when said program runs on a computer.

Another subject of the invention is a computer program product, in particular for the implementation of the method such as is defined above, characterized in that it comprises program code means, stored on a medium readable by a computer, in order to carry out the totality of the steps of the algorithm(s) A1) and/or A2) such as is/are defined hereinabove, when said program product runs on a computer.

The software according to the invention could be included on its own or in combination with other surveillance methods (EEG, evoked potentials, etc.) in a feedback loop for adjusting the administration of medications in anesthesia, intensive care, or more generally in medical treatment.

A further subject of the invention is a device, in particular for the implementation of the method according to the invention and such as is defined hereinabove. This device is characterized in that it essentially comprises:

a) means for continuously measuring (beat-by-beat) time intervals between 2 consecutive cardiac cycles (IT) and of the arterial pressure (AP);

b) means for filtering, with a low-pass filter, beat-by-beat series of the time intervals IT and series of AP calculated in step a), in order to eliminate the rapid variations under parasympathetic control, at the upper respiratory frequency or frequency equal to a threshold in the range between 0.1 and 0.15 Hz, this filtering giving rise to filtered series $IT_f$ and $AP_f$ of IT and of AP, respectively;

c) surveillance means for monitoring the concomitant occurrence of a temporary inefficiency of the cardiac baro-reflex and of an activation of the non-baro-reflex cardiovascular regulation via the manifestation of events chosen from the following group of sequences:

increase in $AP_f$/time period/reduced increase in $IT_f$;

increase in $AP_f$/time period/delayed increase in $IT_f$;

increase in $AP_f$/time period/decrease in $IT_f$;

and also the combination of at least two of these sequences;

d) and at least one alarm for warning of the concomitant occurrence of a temporary inefficiency of the cardiac baro-reflex and of an activation of the non-baro-reflex cardiovascular regulation according to step c).

These means, constitutive of the device, are described in more detail hereinbelow, and also in the examples hereinafter.

The device according to the invention can be used in the form of:

i) an additional module that can fit into the existing modular monitors (of the HP®/Philips® or Datex® type);

ii) a software add-on for a simple software update.

In the case a) and b), this device would use the ECG and/or SpO2 signals coupled with the intermittent values of AP available in all operating theaters;

iii) a stand-alone module integrated, for example, into a non-invasive monitor of continuous AP (in this case, the IT series will be the intervals of time between two characteristic points of the AP).

This device can also be used for animals or in the following fields, both during surgery and outside of the operating theater: assistance with diagnosis in real time in cardiology intensive care or in mobile cardiology (forecast of myocardic ischemia, forecast of ventricular fibrillation), anesthesia (post-operative myocardic ischemia, local/regional anesthesia, pain, etc. . . . ), medical or surgical resuscitation (adult, pediatric, neo-natal), obstetrics, accident and emergency medicine, oxyology, medicine in space, functional exploration of the autonomic nervous system (stroke, diabetes, neuro-vegetative dystonia).

EXAMPLE

Clinical Trial

1/Equipment and Methods

A patient (ASA-I, 33 years old) underwent ligamentoplastie surgery of the knee under general anesthesia induced with propofol (DIPRIVAN®) and remifentanil (ULTIVA®). The following cardiovascular signals were continuously recorded during the whole surgical operation: the electrocardiogram (ECG) and the non-invasive arterial pressure (FINAPRES 2300, Ohmeda, Englewood, Colo.). Indices for the depth of the anesthesia derived from the electroencephalogram (EEG) were also continuously recorded throughout the whole of the surgical operation: the BIS® index (Aspect, Natick, Mass., USA), version 2002, and the AAI index (A-Line®), Danmeter A/S, Odense, Denmark). The acquisition of the cardiovascular signals and derivatives of the EEG were carried out by means of a portable computer via an acquisition card (KPC-MCIA 16AIAO, Keithley, Cleveland, Ohio) for the cardiovascular signals and via RS232 serial ports for the signals derived from the EEG. The acquisition, the storage and the processing of the data were carried out by means of the software application RECAN© (Alpha-2, Lyon, France).

Figure 1:
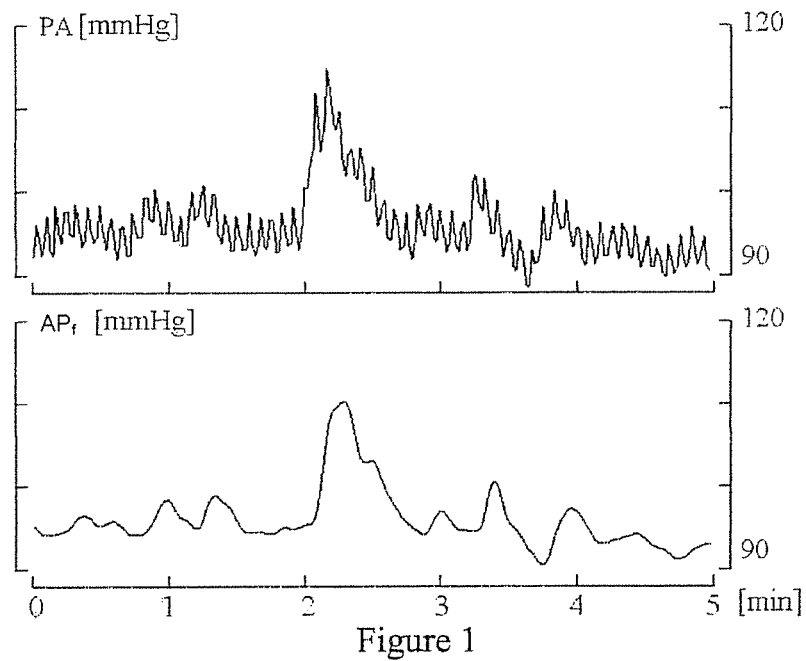
FIG. 1 shows:
a graph of non-invasive arterial pressure series (AP) measured in mm Hg with a FINAPRES 2300, Ohmeda, Englewood, Colo., as a function of time (min);
and a graph of the $AP_f$ series corresponding to the AP series in mm Hg, filtered by means of a low-pass filter, as a function of time (min).
Figure 2:
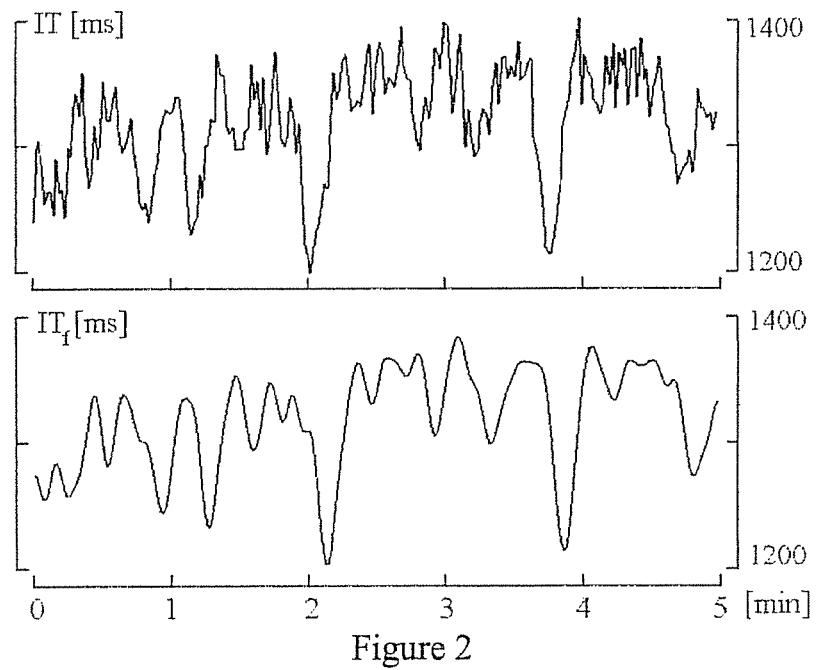
FIG. 2 shows:
a graph of the series of time intervals (IT) in ms, between 2 cardiac cycles, as a function of time (min);
and a graph of the $IT_f$ series corresponding to the IT series in ms, filtered by means of a low-pass filter, as a function of time (min).

The series of time intervals (IT) between 2 cardiac cycles were obtained, beat-by-beat, by calculating the intervals of time (intervals R-R) between two QRS complexes of the ECG. The series of the arterial pressures (AP) were obtained, beat-by-beat, by calculating the systolic arterial pressures for each cardiac cycle. The series of IT and of AP were filtered by means of a low-pass filter with infinite pulse response, here preferably a Butterworth filter whose cut-off frequency was in the range between 0.1 Hz and 0.15 Hz. This filtering generated filtered series $IT_f$ and $AP_f$ in which the respiratory variations under parasympathetic control were eliminated. The filtering of the respiratory variations (here at 0.22 Hz) is illustrated in FIGS. 1 and 2. The local minimum and maximum were detected in the signals $IT_f$ and $AP_f$ and are illustrated by crosses in FIGS. 3 and 4. The amplitude of each rise in $AP_f$ was calculated by taking the difference between each local maximum of $AP_f$ and the preceding local minimum of $AP_f$. For each rise in $AP_f$ whose amplitude was higher than a given threshold in the range between 1 mmHg and 5 mmHg, a procedure for calculating the efficiency of the baro-reflex and non-baro-reflex cardiovascular regulation was launched according to the following. Initially, the following parameters were calculated:

the duration $\Delta T_{AP}$ of the rise in $AP_f$, defined as the difference between the time of said local maximum of $AP_f$ and the time of the preceding local minimum of $AP_f$;

the period called estimation period $P_e$, defined as the duration $\Delta T_{AP}$ of the rise in $AP_f$ multiplied by a coefficient k;

the time delay $\tau$ between said rise in $AP_f$ and the rise in $IT_f$ that has followed this rise in $AP_f$.

Figure 3:
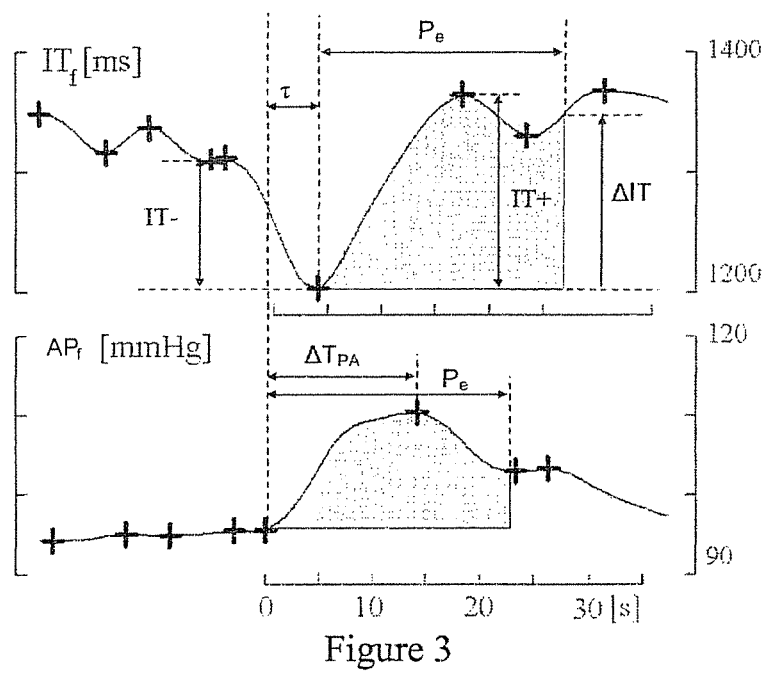
FIG. 3 shows:
a graph of the series of filtered time intervals $IT_f$ according to the method presented in FIG. 2, as a function of time (s);
and a graph of the filtered arterial pressures $AP_f$ series according to the method presented in FIG. 1, as a function of time (s);
measured during normal operation of the cardiac baroreflex.
Figure 4:
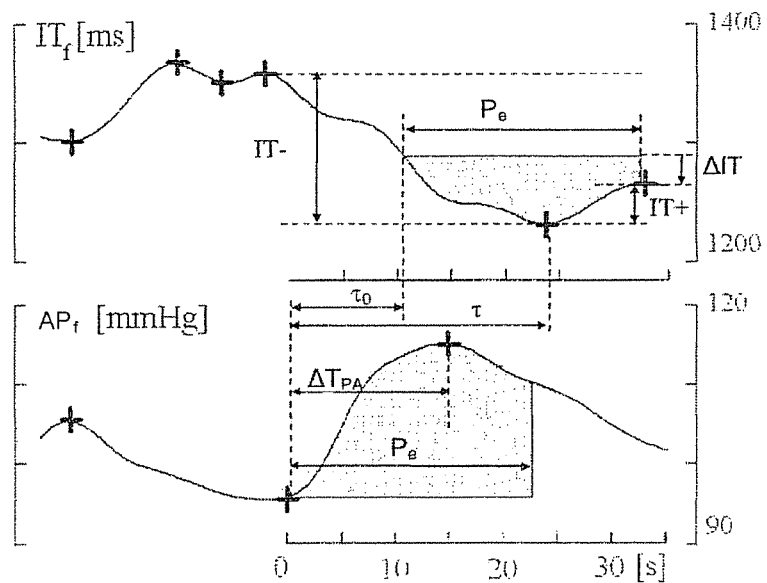
FIG. 4 shows:
a graph of the series of filtered time intervals $IT_f$ according to the method presented in FIG. 2, as a function of time (s);
and a graph of the filtered arterial pressures $AP_f$ series according to the method presented in FIG. 1, as a function of time (s);
measured during abnormal operation of the cardiac baroreflex.

The parameters $\Delta T_{AP}$, $P_e$ and $\tau$ are illustrated in FIGS. 3 and 4.

Depending on the value of the time delay $\tau$, the baro-reflex response of $IT_f$ corresponding to said rise in $AP_f$ was:

either the rise in $IT_f$ that has followed said rise in $AP_f$ if $\tau$ was in the range between a lower limit $t_{inf}$ equal to 0 s and an upper limit $t_{sup}$ in the range between 10 s and 20 s (see FIG. 3);

or the sequence of $IT_f$ that has begun after a pre-defined interval $\tau_0$ in the range between 5 s and 15 s with respect to the start of said rise in $AP_f$ in the case where $\tau$ was higher than the limit $t_{sup}$ in the range between 10 s and 20 s (see FIG. 4).

In both cases, the duration of the baro-reflex response of $IT_f$ is equal to said estimation period $P_e$.

Once the baro-reflex response of $IT_f$ had been identified, the following parameters were calculated:

the area under the curve of said rise in $AP_f$ defined as the sum of the algebraic differences between all the samples of the signal $AP_f$ during the estimation period $P_e$ starting from the beginning of said rise in $AP_f$, and the value of the $AP_f$ at the start of said rise in $AP_f$ (gray shaded area in FIGS. 3 and 4);

the area under the curve of said baro-reflex response of $IT_f$ defined as the sum of the algebraic differences between all the samples of the signal $IT_f$ during the estimation period $P_e$ starting from the beginning of said baro-reflex response of $IT_f$, and the value of $IT_f$ at the start of said baro-reflex response of $IT_f$ (gray shaded area in FIGS. 3 and 4);

the parameter p1 equal to the ratio between the area under the curve of said baro-reflex response of $IT_f$ and the area under the curve of said rise in $AP_f$;

the amplitude IT+ of said baro-reflex response of $IT_f$ defined as the difference between the maximum reached by the $IT_f$ in the course of its rise over the duration of said baro-reflex response of $IT_f$ and the level of $IT_f$ at the start of the rise in $IT_f$ that has followed said rise in $AP_f$ (see FIGS. 3 and 4);

the parameter p2 equal to the amplitude IT− of the fall in $IT_f$ that has preceded the rise in $IT_f$ that has followed said rise in $AP_f$ (see FIGS. 3 and 4);

the parameter p3 equal to the ratio between the amplitude IT+ and the amplitude IT−;

the parameter p4 equal to the algebraic difference $\Delta IT$ between the value of $IT_f$ after said estimation period $P_e$ starting from the beginning of said baro-reflex response of $IT_f$ and the value of $IT_f$ at the start of said baro-reflex response of $IT_f$ (see FIGS. 3 and 4).

According to a preferred embodiment, the surveillance of the concomitant occurrence of a temporary inefficiency of the cardiac baro-reflex and of an activation of the non-baro-reflex cardiovascular regulation was carried out by comparing the parameters p1-p4 with pre-defined thresholds. An index for the depth of the anesthesia, notably of the analgesic component, called CARDEAN (CARdiovascular DEpth of ANesthesia) was calculated. According to a preferred embodiment, the CARDEAN index was designed to take values between 0 and 100, the CARDEAN value increasing with the lightening of the anesthesia. According to this preferred embodiment, the CARDEAN index was designed to take values strictly greater than 60 if at least the 4 following conditions have been met:

1) the parameter p1 has been below a threshold s1 preferably in the range between 1 and 3,
2) the parameter p2 has been above a threshold s2 preferably in the range between 40 ms and 80 ms,
3) the parameter p3 has been below a threshold s3 preferably in the range between 0.3 and 0.75,
4) the parameter p4 has been below a threshold s4 preferably in the range between −20 and 10.

An alarm warning of the lightening of the anesthesia, notably of the analgesic component, was emitted each time that the CARDEAN index was strictly greater than 60.

FIGS. 3 and 4 illustrate the algorithm for calculating the CARDEAN index.

FIG. 3 shows the normal operation of the cardiac baro-reflex corresponding to an adequate anesthesia. The exact values of the parameters described above are as follows:

amplitude of the rise in $AP_f$: 14.56 mmHg
duration $\Delta T_{AP}$ of the rise in $AP_f$: 14 s
coefficient k: 1.64
estimation period $P_e$: $k*\Delta T_{AP}=1.64*14=23$ s
time delay $\tau$ between the rise in $AP_f$ and the rise in $IT_f$ that has followed this rise in $AP_f$: 4 s Since the time delay $\tau$ was in the range between 0 s and an upper limit $t_{sup}$ in the range between 10 s and 20 s, the baro-reflex response of $IT_f$ corresponding to said rise in $AP_f$ was the rise in $IT_f$ that has followed said rise in $AP_f$.

The following parameters were calculated:
area under the curve of said rise in $AP_f$: 231.1 mmHg
area under the curve of said baro-reflex response of $IT_f$: 2512.6 ms
the parameter p1 equal to the ratio between the area under the curve of said baro-reflex response of $IT_f$ and the area under the curve of said rise in $AP_f$:

$p1=2512.6/231.1=10.886$ amplitude IT+ of said baro-reflex response of $IT_f$: 159.78 ms
the parameter p2 equal to the amplitude IT− of the fall in $IT_f$ that has preceded the rise in $IT_f$ that has followed said rise in $AP_f$:

$p2=106.01$ ms the parameter p3 equal to the ratio between the amplitude IT+ and the amplitude IT−:

$p3=159.78/106.01=1.507$ the parameter p4 equal to the algebraic difference $\Delta IT$ between the level of $IT_f$ at the end of the estimation period shaded in gray and the level of $IT_f$ at the start of said baro-reflex response of $IT_f$:

$p4=141.34$ ms

The parameter p1=10.886 has not been below the threshold s1 preferably in the range between 1 and 3.

The parameter p2=106.01 ms has been above the threshold s2 preferably in the range between 40 ms and 80 ms.

The parameter p3=1.507 has not been below the threshold s3 preferably in the range between 0.3 and 0.75.

The parameter p4=141.34 has not been below the threshold s4 preferably in the range between −20 and 10.

Consequently, of all the 4 conditions necessary for the triggering of the alarm for lightening of anesthesia, only the second condition was met. Thus, the CARDEAN index was strictly lower than 60 and the alarm was not triggered.

FIG. 4 shows the abnormal operation of the cardiac baro-reflex, specified by the concomitant occurrence of a temporary inefficiency of the cardiac baro-reflex, and of an activation of the non-baro-reflex cardiovascular regulation. This corresponds to a lightening of the anesthesia, notably of the analgesic component. The exact values of the parameters described above are as follows:

amplitude of the rise in $AP_f$: 19.35 mmHg
duration $\Delta T_{AP}$ of the rise in $AP_f$: 15 s
coefficient k: 1.53
estimation period $P_e$: $k*\Delta T_{AP}=1.53*15=23$ s
time delay τ between the rise in $AP_f$ and the rise in $IT_f$ that has followed this rise in $AP_f$: 24 s Since the time delay τ was higher than limit $t_{sup}$ in the range between 10 s and 20 s, the baro-reflex response of $IT_f$ corresponding to said rise in $AP_f$ was the sequence of $IT_f$ that has begun after a pre-defined interval $\tau_0$ in the range between 55 and 155 with respect to the start of said rise in $AP_f$.

The following parameters were calculated:
area under the curve of said rise in $AP_f$: 325.06 mmHg
area under the curve of said baro-reflex response of $IT_f$: −823.9 ms
the parameter p1 equal to the ratio between the area under the curve of said baro-reflex response of $IT_f$ and the area under the curve of said rise in $AP_f$:

$$p1=-823.9/325.06=-2.54$$

amplitude IT+ of said baro-reflex response of $IT_f$: 34.53 ms
the parameter p2 equal to the amplitude IT− of the fall in $IT_f$ that has preceded the rise in $IT_f$ that has followed said rise in $AP_f$:

$$p2=126.43 \text{ ms}$$

the parameter p3 equal to the ratio between the amplitude IT+ and the amplitude IT−:

$$p3=34.53/124.43=0.27$$

the parameter p4 equal to the algebraic difference ΔIT between the level of $IT_f$ at the end of the estimation period shaded in gray and the level of $IT_f$ at the start of said baro-reflex response of $IT_f$:

$$p4=-20.36 \text{ ms}$$

The parameter p1=−2.54 has been below the threshold s1 preferably in the range between 1 and 3.

The parameter p2=126.43 ms has been above the threshold s2 preferably in the range between 40 ms and 80 ms.

The parameter p3=0.27 has been below the threshold s3 preferably in the range between 0.3 and 0.75.

The parameter p4=−20.36 has been below the threshold s4 preferably in the range between −20 and 10.

Consequently, all the 4 conditions necessary for the triggering of the alarm for lightening of anesthesia were met. Thus, the CARDEAN index was strictly greater than 60 and the alarm was triggered.

2/Experimental Protocol

The anesthesiologist was working blind with respect to the index for the depth of the anesthesia derived from the electroencephalogram (EEG), here the indices BIS and AAI. The anesthesiologist was guided solely by the usual clinical criteria: hypertension, tachycardia, movement, coughing. The recording of the cardiovascular signals and of the indices derived from the EEG began at t=0 min (see FIG. 5). The induction of the anesthesia took place at t=6 min. At t=11 min, the patient was already anesthetized and all the Guedel indicators were inhibited, namely the ciliar reflex, the corneal reflex, the lacrimation, the eye movement and the motor response to the nociceptive stimulation. It is from this moment on that the CARDEAN index was applicable. The intubation took place at t=12.92 min. The patient coughed for about 30 s after the intubation. The surgery commenced at t=28.96 min. At t=29.95 min, the patient started to move in an unexpected manner for about one minute, preventing the continuation of the operation (see FIG. 6). The anesthetic was stopped at t=86.46 min. The patient coughed at t=87.87 min and at t=98.79 min. The patient opened his eyes immediately after the verbal stimulation at t=99.14 min. The patient was extubated in the operating theater at t=99.8 min.

The alarm threshold for the BIS index was fixed at 55%. The alarm threshold for the AAI index was fixed at 37%. The alarm threshold for the CARDEAN index was fixed at 60%.

3/Results

All the signs of waking (movement, opening of the eyes, coughing) were associated with an increase in the CARDEAN index according to the invention above the threshold of 60%. In contrast, these waking signs were not always associated with an increase above the threshold of 55% of the BIS index (coughing at t=12.92 min) or above the threshold of 37% of the AAI index (coughing at t=12.92 min and at t=87.87 min, movement at t=29.95 min). Moreover, the increase in the CARDEAN index according to the invention was more precocious than the increase in the BIS or AAI indices (see FIG. 6). Indeed, the involuntary movement at t=29.95 min was able to be predicted by the CARDEAN index 28 s in advance. In contrast, this movement at t=29.95 min was not able to be predicted by the BIS and AAI indices.

4/Description of the Figures

FIG. 1. Filtering of the series of arterial pressure (AP). The non-invasive AP (FINAPRES 2300, Ohmeda, Englewood, Colo.) was continuously recorded. The AP series (high) were obtained beat-by-beat by calculating the systolic arterial pressures for each cardiac cycle. The AP series were filtered by means of a low-pass filter with infinite pulse response, here preferably a Butterworth filter whose cut-off frequency was in the range between 0.1 Hz and 0.15 Hz. This filtering generated filtered series $AP_f$(low) in which the respiratory variations (0.22 Hz) under parasympathetic control were eliminated.

FIG. 2. Filtering of the series of time intervals (IT). The electrocardiogram (ECG) was continuously recorded. The series of IT (high) between 2 cardiac cycles were obtained beat-by-beat by calculating the time intervals (intervals R-R) between 2 QRS complexes of the ECG. The series of IT were filtered by means of a low-pass filter with infinite pulse response, here preferably a Butterworth filter whose cut-off frequency was in the range between 0.1 Hz and 0.15 Hz. This filtering generated filtered series $IT_f$(low) in which the respiratory variations (0.22 Hz) under parasympathetic control were eliminated.

FIG. 3. Normal operation of the cardiac baro-reflex. Series of filtered time intervals $IT_f$(high) and filtered arterial pressures $AP_f$(low) according to the method presented in FIGS. 1 and 2. At the moment t=0, a rise in $AP_f$ takes place (gray shaded region). This rise in $AP_f$ is followed after a time delay τ (here around 4 s) by a rise in the $IT_f$. Since the time delay τ was less than a limit in the range between 10 s and 20 s, the baro-reflex response of $IT_f$ corresponding to said rise in $AP_f$ was the rise in $IT_f$ that has followed said rise in $AP_f$ (gray shaded region). $\Delta T_{AP}$: time delay of said rise in $AP_f$. $P_e$: period called estimation period equal to the time delay $\Delta T_{AP}$ multiplied by a coefficient k. IT+: amplitude of said baro-reflex response of $IT_f$. IT−: amplitude of the fall in $IT_f$ that has preceded said rise in $IT_f$. ΔIT: algebraic difference between the level of $IT_f$ at the end of the estimation period shaded in gray and the level of $IT_f$ at the start of said baro-reflex response of $IT_f$. This figure shows an efficient operation of the cardiac baro-reflex because said baro-reflex response was fast and of large amplitude. In this case, the depth of the anesthesia is considered as being adequate by the CARDEAN index according to the invention. The depth of the anesthesia was also adequate according to the conventional clinical signs: absence of spontaneous movement, absence of motor response to a painful stimulus, absence of ciliar and corneal reflexes, pupils centered and fixed.

FIG. 4. Abnormal operation of the cardiac baro-reflex. Series of filtered time intervals $IT_f$ (high) and of filtered arterial pressures $AP_f$ (low) according to the method displayed in FIGS. 1 and 2. At time t=0, a rise in $AP_f$ takes place (gray shaded area). This rise in $AP_f$ is followed after a time delay τ (here around 24 s) by a rise in the $IT_f$. Since the time delay τ was greater than a limit in the range between 10 s and 20 s, the baro-reflex response of $IT_f$ corresponding to said rise in $AP_f$ was the sequence of $IT_f$ that has begun after a pre-defined interval $\tau_0$ in the range between 5 s and 15 s with respect to the start of said rise in $AP_f$ (gray shaded region). $\Delta T_{PA}$: time delay of said rise in $AP_f$. $P_e$: period called estimation period equal to the time delay $\Delta T_{PA}$ multiplied by a coefficient k. IT+: amplitude of said baro-reflex response of $IT_f$. IT−: amplitude of the fall in $IT_f$ that has preceded said rise in the $IT_f$. ΔIT: algebraic difference between the level of $IT_f$ at the end of the estimation period shaded in gray and the level of $IT_f$ at the start of said baro-reflex response of $IT_f$. This figure demonstrates the concomitant occurrence of a temporary inefficiency of the cardiac baro-reflex and of an activation of the non-baro-reflex cardiovascular regulation. Indeed, said baro-reflex response has been delayed and is of low amplitude, leaving room for a non-baro-reflex tachycardia. In this case, the depth of the anesthesia is considered as inadequate by the CARDEAN index according to the invention. The depth of the anesthesia turned out to be inadequate because an involuntary movement of the patient took place approximately 28 s later. The CARDEAN index according to the invention was able to predict this accidental "waking".

Figure 5:
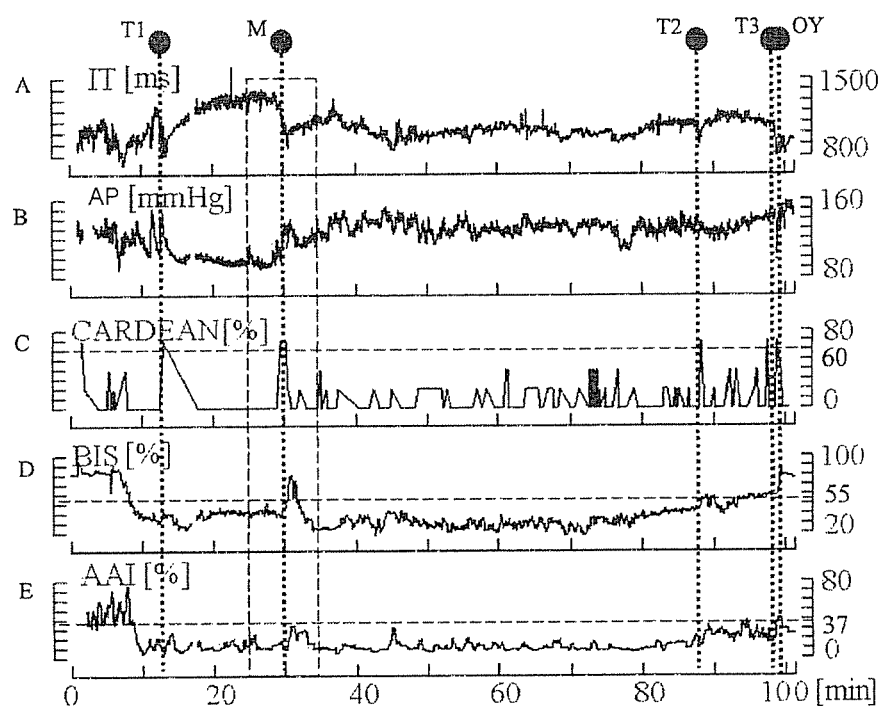
FIG. 5 shows:
a graph A of continuous recording of the time intervals IT, as a function of time (min);
a graph B of continuous recording of the arterial pressures AP, as a function of time (min);
a graph C of continuous recording of the CARDEAN index according to the invention, as a function of time (min);
a graph D of continuous recording of the BIS index, as a function of time (min);
and a graph E of continuous recording of the AAI index, as a function of time (min);
during a surgical procedure under general anesthesia.

FIG. 5. Comparison of the CARDEAN index according to the invention with the BIS and AAI indices. Continuous recording of the time intervals IT (A), of the arterial pressures AP (B) and of the CARDEAN (C), BIS (D) and AAI (AAI) indices in the course of a surgical procedure under general anesthesia. The induction of the anesthesia took place at t=6 min. The intubation took place at t=12.92 min. The patient coughed for around 30 s after the intubation (dashed line: "T1"). The surgery began at t=28.96 min. At t=29.95 min, the patient began to move in an unexpected manner for around 1 minute, preventing the operation from continuing (dotted line: "M"). The period between t=25 min and t=35 min (dotted rectangle) is enlarged in FIG. 6. The anesthetic was stopped at t=86.46 min. The patient coughed at t=87.87 min (dotted line: "T2") and at t=98.79 min (dotted line: "T3"). The patient opened his eyes immediately after the verbal stimulation at t=99.14 min (dotted red line: "OY"). The patient was extubated in the operating theater at t=99.8 min. The alarm thresholds for the BIS, AAI and CARDEAN indices were respectively fixed at 55%, 37% and 60% (horizontal dotted lines). The CARDEAN index crossed the alarm threshold for all the waking signs (movement, opening of the eyes, coughing). In contrast, the BIS and AAI indices did not cross the alarm threshold for the following waking signs: couching at t=12.92 min (BIS and AAI), coughing at t=87.87 min (AAI) and movement at t=29.95 min (AAI).

Figure 6:
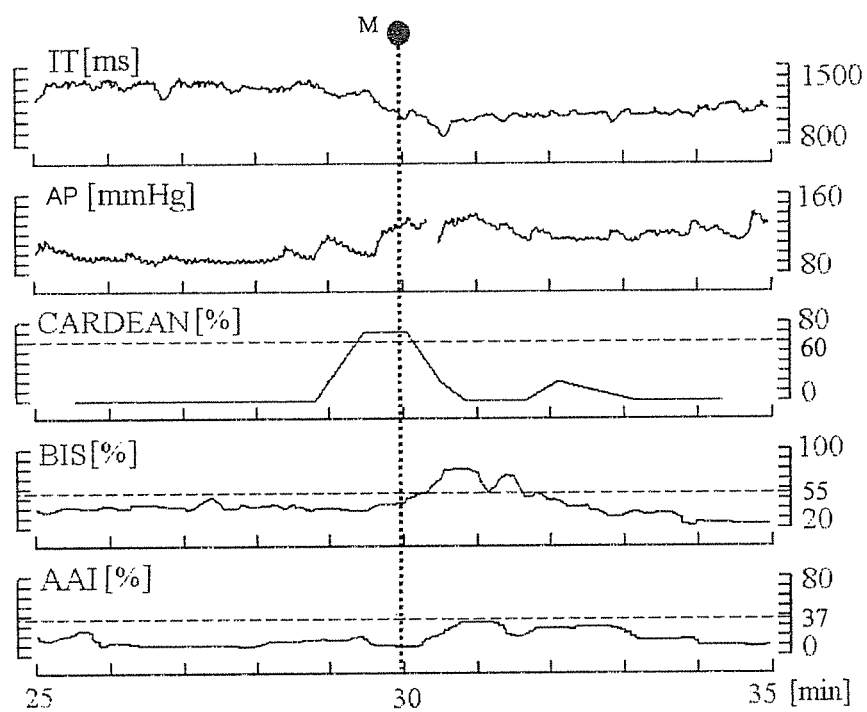
FIG. 6 shows:
a graph of continuous recording of the time intervals IT, as a function of time (min);
a graph of continuous recording of the arterial pressures AP, as a function of time (min);
a graph of continuous recording of the CARDEAN index according to the invention, as a function of time (min);
a graph of continuous recording of the BIS index, as a function of time (min);
and a graph of continuous recording of the AAI index, as a function of time (min);
during a surgical procedure under general anesthesia with an involuntary movement.

FIG. 6. Comparison of the CARDEAN index according to the invention with the BIS and AAI indices. Enlargement of FIG. 6 between t=25 min and t=35 min showing in more detail the movement that took place at t=29.95 min (dotted line: "M"). The alarm thresholds for the BIS, AAI and CARDEAN indices were respectively fixed at 55%, 37% and 60% (horizontal dotted lines). The only index that crossed the alarm threshold before the movement was the CARDEAN index. The involuntary movement at t=29.95 min was able to be predicted by the CARDEAN index approximately 28 s in advance. In contrast, this movement at t=29.95 min was not able to be predicted by the BIS and AAI indices.

Figure 7:
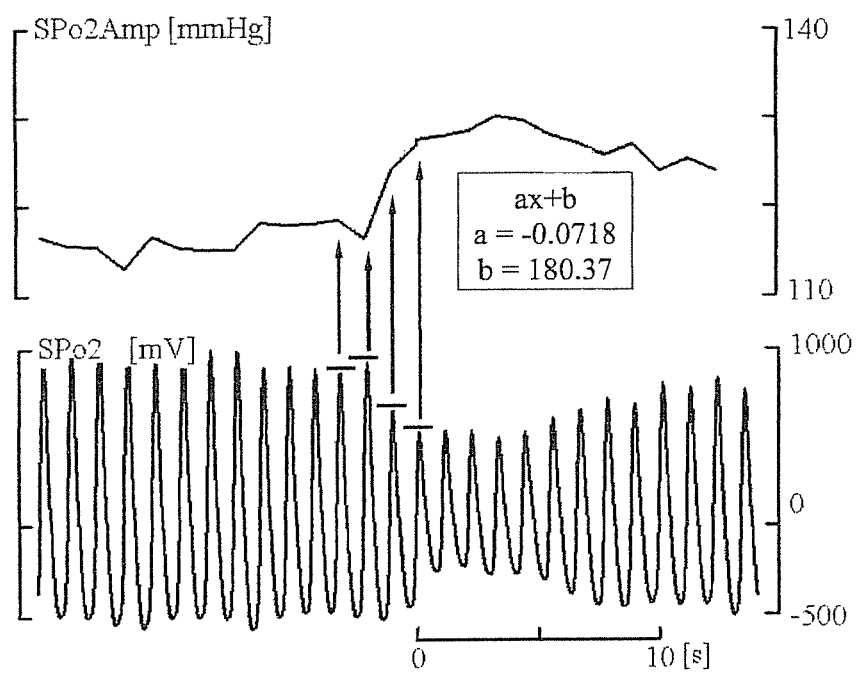
FIG. 7 shows:
a graph of the wave of the continuous oxygen saturation of the blood (SpO2), as a function of time (s);
and a graph of a series of the values (SpO2Amp) corresponding to the transformation of the amplitude of each maximum of the SpO2 signal, by means of a linear operator of the $1^{st}$ degree (ax+b), as a function of time (s)

FIG. 7. Transformation of the wave of the continuous oxygen saturation of the blood (SpO2) (low) in a series of the values (SpO2Amp) (high) which is approaching the series of the beat-by-beat arterial pressures (AP). The method consists in detecting the maxima of the signal SpO2 for each cardiac cycle (horizontal lines) and in transforming the amplitude of each maximum by means of a linear operator of the $1^{st}$ degree (ax+b). The coefficients of the linear operator (a and b) were calculated from the intermittent values of systolic AP measured by means of a blood-pressure armband.

Figure 8:
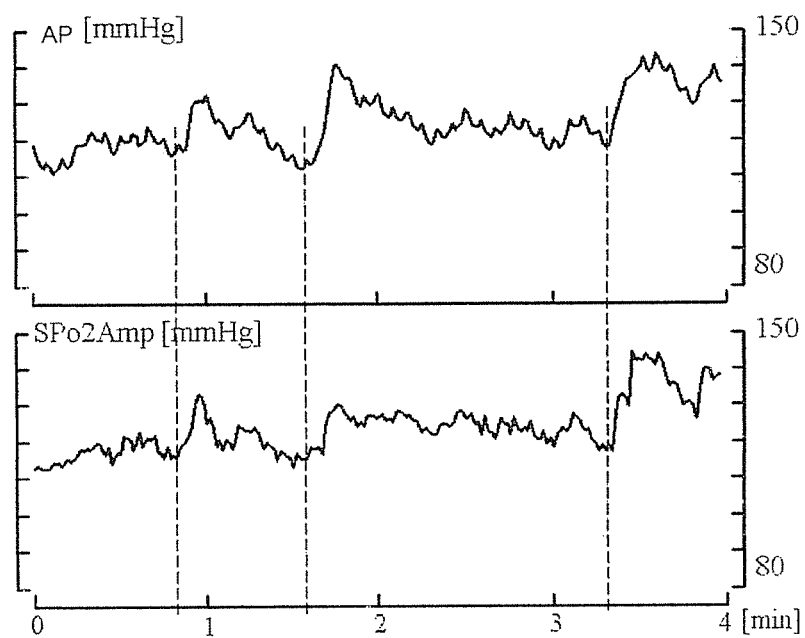
FIG. 8 shows:
a graph of non-invasive arterial pressure series (AP) measured in mm Hg with a FINAPRES 2300, Ohmeda, Englewood, Colo., as a function of time (min);
and a graph of a series of the values (SpO2Amp) of FIG. 7, as a function of time (min).

FIG. 8. Comparison of the series of systolic AP (high) obtained by means of a non-invasive measurement apparatus (FINAPRES 2300, Ohmeda, Englewood, Colo.) with the series of the systolic AP (SpO2Amp) (low) indirectly obtained from the wave of the continuous oxygen saturation of the blood (SpO2) (see FIG. 7). The 2 series of AP exhibit similar variations. Moreover, the start points of the rises in AP are concomitant on the 2 series of AP (dotted lines).

The invention claimed is:

1. A method for predicting abnormal medical events, assisting in diagnosis, or monitoring a patient, comprising detecting and simultaneously distinguishing between, continuously and in real time, a concomitant occurrence of a temporary inefficiency of the cardiac baro-reflex and an activation of the non-baro-reflex cardiovascular regulation, wherein the detecting and simultaneously distinguishing is carried out using a device comprising a computing unit; and wherein the detecting and simultaneous distinguishing comprises:
   a) continuously measuring (beat-by-beat) time intervals determined from an ECG between two consecutive cardiac cycles (IT) and arterial pressure (AP); and
   b) filtering by means of a low-pass filter the beat-by-beat series of the time intervals IT and the series of AP calculated at step a), the filtering giving rise to filtered series $IT_f$ and $AP_f$ of IT and of AP respectively; and
   c) monitoring for the occurrence of one or more of the following sequences:
     (i) increase in $AP_f$/time period/reduced increase in $IT_f$;
     (ii) increase in $AP_f$/time period/delayed increase in $IT_f$; and
     (iii) increase in $AP_f$/time period/decrease in $IT_f$;
   wherein the occurrence of any one of (i)-(iii) is a predictive index that indicates (a) the concomitant occurrence of a temporary inefficiency of the cardiac baro-reflex and an activation of the non-baro-reflex cardiovascular regulation and (b) the cardiovascular depth of anesthesia.

2. The method of claim 1, wherein the time intervals IT are calculated either from
   a) intervals of time between two QRS complexes from the ECG (RR), or
   b) intervals between two points that are characteristic of continuous AP or of continuous oxygen saturation level of the blood (SpO2).

3. The method of claim 1, wherein the AP is chosen from the group of signals comprising: systolic arterial pressure (SAP) of the patient, diastolic arterial pressure (DAP) of the patient, and mean arterial pressure (MAP) of the patient, each of which pressures are determined from the ECG.

4. The method of claim 1, wherein the AP is obtained either by direct invasive or non-invasive measurement, or by indirect measurement.

5. The method of claim 1, wherein the AP obtained indirectly, by measuring the continuous SpO2 calibrated with the intermittent values of AP, wherein the measuring comprises:
   a1) calculating the series of the maxima of the SpO2 signal during each cardiac cycle;
   a2) inverting the series obtained at step a1) by subtracting from a constant strictly higher than the maximum amplitude of the SpO2 signal; and
   a3) calibrating the series obtained at step a2) in units of pressure by applying a linear operator of the 1st degree to the series obtained at step a2), the coefficients of this operator being obtained from the intermittent values of AP.

6. The method of claim 1, wherein the filtering is carried out in real time by at least one filter with infinite impulse response (RII) or with finite impulse response.

7. The method of claim 1, wherein at least one of the following signals is displayed on at least one screen: the series of IT and of AP obtained according to a) and the series of $IT_f$ and $AP_f$ obtained according to b).

8. The method of claim 1, wherein the concomitant occurrence of a temporary inefficiency of the cardiac baro-reflex and an activation of the non-baro-reflex cardiovascular regulation
is indicated by one or more of the following parameters:
   p1) a ratio between the area under the curve of a sequence of $IT_f$ called baro-reflex response of $IT_f$ and the area under the curve of the rise in $AP_f$ which has caused said baro-reflex response of $IT_f$;
   p2) an amplitude of the fall in $IT_f$ which has preceded the rise in $IT_f$ that follows said rise in $AP_f$;
   p3) a ratio between the amplitude of said baro-reflex response of $IT_f$ and the amplitude of said fall in $IT_f$;
   p4) an algebraic difference $\Delta IT$ between the value of $IT_f$ after a period of time referred to as estimation time starting from the beginning of said baro-reflex response of $IT_f$ and the value of $IT_f$ at the end of said baro-reflex response of $IT_f$.

9. The method of claim 8, wherein said baro-reflex response of $IT_f$ caused by said rise in $AP_f$ is:
   either the rise in $IT_f$ that follows said rise in $AP_f$ if said rise in $IT_f$ begins within an interval of time included between a lower limit equal to 0 s and an upper limit included between 10 s and 20 s with respect to the start of said rise in $AP_f$;
   or the sequence of $IT_f$ which begins after an interval of time included between 5 s and 15 s with respect to the start of said rise in $AP_f$ in the case where the rise in $IT_f$ that follows said rise in $AP_f$ begins after said upper limit in the range between 10 s and 20 s with respect to the start of said rise in $AP_f$;

in both cases, the duration of the baro-reflex response of $IT_f$ being equal to said estimation time; the amplitude of said baro-reflex response of $IT_f$ being the difference between the maximum reached by the $IT_f$ in the course of its rise over the duration of said baro-reflex response of $IT_f$ and the level of $IT_f$ at the start of the rise in $IT_f$ that follows said rise in $AP_f$.

10. The method of claim 9, wherein the only rises in $AP_f$ taken into consideration are those whose amplitude is higher than a pressure threshold in the range between 1 mmHg and 5 mmHg.

11. The method of claim 8, wherein the period called estimation period is equal to the duration of said rise in $AP_f$ multiplied by a coefficient in the range between 0.5 and 2.

12. The method of claim 8, wherein said areas under the curves of the baro-reflex response of $IT_f$ and of the rise of $AP_f$ are calculated between a time called reference time and during said estimation time, by performing, for each sample of said curve in the course of said estimation time starting from said reference time, the sum of the algebraic differences between the value of the sample at a given moment and the value of the curve at said reference time.

13. The method of claim 1, wherein at least one alarm is designed to predict any lightening, programmed or inopportune, of the anesthesia, comprising means for displaying the alarm designed to warn of the concomitant occurrence of a temporary inefficiency of the cardiac baro-reflex and an activation of the non-baro-reflex cardiovascular regulation, by continuously displaying in real time a predictive index expressing the cardiovascular depth of the anesthesia.

14. The method of claim 8, wherein step c) of the surveillance for the concomitant occurrence of a temporary inefficiency of the cardiac baro-reflex and an activation of the non-baro-reflex cardiovascular regulation, together with the emission of an alarm according to step d), are alternately governed by at least one of the following sequences of steps:
   A1) the predictive index expressing the cardiovascular depth of the anesthesia indicates a lightening of the anesthesia and emits an alarm when at least the four following conditions are met:
      the ratio parameter p1 is below a value in the range between 0 and 4,
      the amplitude parameter p2 is above a value in the range between 30 ms and 300 ms,
      the ratio parameter p3 is below a value in the range between 0 and 1, and
      the algebraic difference parameter p4 is below a value in the range between −100 and 25,
   A2) the predictive index, expressing the cardiovascular depth of the anesthesia and indicating a lightening of the anesthesia, is obtained by using a neural network having as input parameters the parameters of p1 to p4, and having learning conditions so as to obtain an optimal combination of sensitivity and specificity, by means of an ROC (Receiver Operator Characteristic) curve.

15. A computer-readable medium having computer-executable instructions embodied therein for predicting abnormal medical events, assisting in diagnosis, or monitoring a patient, the computer-executable instructions implement the method of claim 8.

16. A computer-readable medium having computer-executable instructions embodied therein for predicting abnormal medical events, assisting in diagnosis, or monitoring a patient, the computer-executable instructions implement the method of claim 14.

\* \* \* \* \*